US007262027B2

(12) United States Patent
Cole et al.

(10) Patent No.: US 7,262,027 B2
(45) Date of Patent: Aug. 28, 2007

(54) **POLYPEPTIDE AND DNA IMMUNIZATION AGAINST *COCCIDIOIDES SPP.* INFECTIONS**

(75) Inventors: Garry T. Cole, Toledo, OH (US); Jieh-Juen Yu, Toledo, OH (US); Jianmin Xue, Toledo, OH (US); Chiung-Yu Hung, Toledo, OH (US); Kalpathi R. Seshan, Toledo, OH (US); Theo N. Kirkland, III, La Jolla, CA (US)

(73) Assignees: Medical College of Ohio, Toledo, OH (US); The Regents of the University of California, Oakland, CA (US); United States of America Represented by the Department of Veterans Affairs, Washington, DC (US)

( * ) Notice: Subject to any disclaimer, the term of this patent is extended or adjusted under 35 U.S.C. 154(b) by 42 days.

(21) Appl. No.: 10/794,287

(22) Filed: Mar. 3, 2004

(65) Prior Publication Data

US 2004/0181046 A1 Sep. 16, 2004

Related U.S. Application Data

(60) Provisional application No. 60/455,221, filed on Mar. 14, 2003.

(51) Int. Cl.
*C12P 21/06* (2006.01)

(52) U.S. Cl. .................. 435/69.1; 536/23.7; 536/24.1; 536/24.2; 435/252.3; 435/320.1; 435/254.1; 435/254.11

(58) Field of Classification Search ............... 536/23.7, 536/24.1, 24.2; 435/69.1, 252.3, 320.1, 254.1, 435/254.11
See application file for complete search history.

(56) References Cited

U.S. PATENT DOCUMENTS 5,583,112 A 12/1996 Kensil et al.
5,589,466 A 12/1996 Felgner et al.
5,703,055 A 12/1997 Felgner et al.
5,843,742 A 12/1998 Natsoulis et al.
5,865,796 A 2/1999 McCabe
6,165,993 A 12/2000 Herrmann et al.
6,183,750 B1 2/2001 Paoletti
6,214,353 B1 4/2001 Paoletti et al.
6,228,371 B1 5/2001 Nano
6,239,116 B1 5/2001 Krieg et al.
6,284,533 B1 9/2001 Thomas
6,287,570 B1 9/2001 Foley
6,339,068 B1 1/2002 Krieg
6,384,018 B1 5/2002 Content et al.
6,403,370 B1 6/2002 Alemany et al.
6,410,010 B1 6/2002 Zhang et al.

OTHER PUBLICATIONS

Pan et al (Infect. Immun. 1995. 63(10): 3994-4002).*
Sambrook et al (Molecular Cloning: A Laboratory Manual, Third Edition, Cold Spring Harbor Laboratory Press, 2001).*
Cole, G.T. et al. (1986) "Antigen identification in *Coccidioides immitis.*" *Microbiology—1986*, I.L. Leive, P.F. Bonventre, J.A. Morella, S.D. Silver, and H.C. Wu (eds.), American Society for Microbiology, Washington, D.C., pp. 159-164.
Cole, G.T. et al. (May 1989) "Isolation of antigens with proteolytic activity from *Coccidioides immitis.*" *Infection and Immunity*, 57(5):1524-1534.
GenBank AY158466 (Nov. 26, 2002) *Coccidioides posadasii* CS antigen (CSA) gene, complete cds, GenBank accession No. AY158466, 2 pages.

* cited by examiner

*Primary Examiner*—Jennifer Graser
(74) *Attorney, Agent, or Firm*—Morrison & Foerster LLP

(57) ABSTRACT

The present invention provides compositions of novel polypeptides and polynucleotides encoding the polypeptides, which polypeptides are useful for generating an immunological response in an individual and in therapeutic application of *Coccidioides* spp. infection.

25 Claims, 2 Drawing Sheets

FIGURE 1. Genomic and amino acid sequences of the Coccidioides spp. CSA gene and protein

```
-256 gaggttctgaagacatttgtgatatttgcgaaggtctattatcggaattgctatcacact
-196 tacccggttgcagaccgggagagggcctgcgttgaggtatataaacctcgatcatgtctc
-136 gcctggagcacatccttctcatcacattcccaacggatatcacgactaagatttaatcag
 -76 aacccttgagaaactttcttataccttcacctctccgacacacttcctccataacaaaac
 -16 tctaaaatcgggaaagATGAAGTTCTCACTCCTCAGCGCTATCGCAGCGGCTGTCTTCGT
   1                 M  K  F  S  L  L  S  A  I  A  A  A  V  F  V 45 CCCTTTCACATCCGCCACTCCACTTGCTAGCACGGCCGACCTCAGCTACGACACTCACTA
  16  P  F  T  S  A  T  P  L  A  S  T  A  D  L  S  Y  D  T  H  Y 105 CGATGACCCATCCCTGCCCCTGAGTGGCGTCACCTGTTCTGACGGGGACAATGGCATGAT
  36  D  D  P  S  L  P  L  S  G  V  T  C  S  D  G  D  N  G  M  I 165 AACAAAGGGCTACAACACCGCCGGCGAGATACCAAACTACCCTCACGTCGGAGGAGCTTT
  56  T  K  G  Y  N  T  A  G  E  I  P  N  Y  P  H  V  G  G  A  F 225 TACGGTCGAAACGTGGAACAGCCCCAACTGTGGAAAGTGCTACAAAGTGACATACAATGC
  76  T  V  E  T  W  N  S  P  N  C  G  K  C  Y  K  V  T  Y  N  A 285 TAAAACGATTTTTTTTGACTGCGATCGACCACAGCAACTCCGGATTTAATATCGCGAAGAA
  96  K  T  I  F  L  T  A  I  D  H  S  N  S  G  F  N  I  A  K  K 345 GTCGATGGACGTATTGACGAACGGACGGGCAGAGGAATTGGGCAGGATCAAGGTGACCTA
 116  S  M  D  V  L  T  N  G  R  A  E  E  L  G  R  I  K  V  T  Y 405 CGAAGAGGTCGCCTCGTCGTTGTGCGGGTTGAAATAAaggcgtattggtcgacgtgccgc
 136  E  E  V  A  S  S  L  C  G  L  K  *  (SEQ ID NO:2)

465 aatgctgagtgcgatgatttgatatttgtttggttgaaggggaggaaccttaatgttaaa
 525 cggttttctttacatttgtaatgcatgtggcgagggatatatgattactcgactggatta
 585 taatatctaatgctaaatttcgaggtttatcggggactccgggtcagcct(SEQ ID NO:8)
```

FIGURE 2. Nucleotide and amino acid sequences of the recombinant CSA gene and protein

```
  1 ATGGGCAGCAGCCATCATCATCATCATCACAGCAGCGGCCTGGTGCCGCGCGGCAGCCAT
  1  M  G  S  S  H  H  H  H  H  H  S  S  G  L  V  P  R  G  S  H

61 ATGAAGTTCTCACTCCTCAGCGCTATCGCAGCGGCTGTCTTCGTCCCTTTCACATCCGCC
 21  M  K  F  S  L  L  S  A  I  A  A  A  V  F  V  P  F  T  S  A

121 ACTCCACTTGCTAGCACGGCCGACCTCAGCTACGACACTCACTACGATGACCCATCCCTG
 41  T  P  L  A  S  T  A  D  L  S  Y  D  T  H  Y  D  D  P  S  L

181 CCCCTGAGTGGCGTCACCTGTTCTGACGGGGACAATGGCATGATAACAAAGGGCTACAAC
 61  P  L  S  G  V  T  C  S  D  G  D  N  G  M  I  T  K  G  Y  N

241 ACCGCCGGCGAGATACCAAACTACCCTCACGTCGGAGGAGCTTTTACGGTCGAAACGTGG
 81  T  A  G  E  I  P  N  Y  P  H  V  G  G  A  F  T  V  E  T  W

301 AACAGCCCCAACTGTGGAAAGTGCTACAAAGTGACATACAATGCTAAAACGATTTTTTTG
101  N  S  P  N  C  G  K  C  Y  K  V  T  Y  N  A  K  T  I  F  L

361 ACTGCGATCGACCACAGCAACTCCGGATTTAATATCGCGAAGAAGTCGATGGACGTATTG
121  T  A  I  D  H  S  N  S  G  F  N  I  A  K  K  S  M  D  V  L

421 ACGAACGGACGGGCAGAGGAATTGGGCAGGATCAAGGTGACCTACGAAGAGGTCGCCTCG
141  T  N  G  R  A  E  E  L  G  R  I  K  V  T  Y  E  E  V  A  S

481 TCGTTGTGCGGGTTGAAATAA (SEQ ID NO: 3)
161  S  L  C  G  L  K  *  (SEQ ID NO: 4)
```

POLYPEPTIDE AND DNA IMMUNIZATION AGAINST *COCCIDIOIDES SPP.* INFECTIONS

RELATED APPLICATIONS

The present application claims priority to U.S. Application Ser. No. 60/455,221 filed Mar. 14, 2003, which is hereby incorporated by reference in its entirety.

STATEMENT REGARDING FEDERALLY FUNDED PROJECT

The United States Government owns rights in the present invention pursuant to Public Service Grants "Immunoreactive Macromolecules of *Coccidioides* Cell Types" (AI19149) and "Isolation and Expression of *Coccidioides* T-cell Antigens" (AI37232) from the National Institutes of Allergy and Infectious Diseases, National Institutes of Health.

FIELD OF THE INVENTION

The present invention relates generally to the fields of pathogenic fungi and immunology. More particularly, the invention provides compositions of *Coccidioides* spp. polypeptide antigens and polynucleotides encoding the polypeptides. In particular, this invention provides novel *Coccidioides*-specific antigens (Csa) and polynucleotides encoding the Csa antigens which are useful for generating or detecting an immunological response and in vaccines and therapeutic applications for infections due to pathogenic *Coccidioides* spp. fungi, such as *C. posadasii* or *C. immitis*.

BACKGROUND OF THE INVENTION

Coccidioidomycosis, otherwise known as the San Joaquin Valley Fever, is a fungal respiratory disease of humans and wild and domestic animals which is endemic to southwestern United States, northern Mexico, and numerous semiarid areas of Central and South America (Pappagianis, D. Epidemiology of Coccidioidomycosis. Current Topics in Medical Mycology. 1988. 2:199-23). Infection occurs by inhalation of airborne spores (arthroconidia) produced by the saprobic phase of *Coccidioides* spp. which grows in alkaline desert soil. *C. immitis* was the first described species, and is now becoming known as the Californian species. The *C. posadasii* species was recently defined, and was previously recognized as the non-Californian population of *C. immitis* (Fisher, M. C., Koenig, G. L., White, T. J., Taylor, J. W. Molecular and phenotypic description of *Coccidioides posadasii* sp. nov., previously recognized as the non-California population of *Coccidioides immitis*. Mycologia 2002. 94(1): 73-84, 2002). The differences in the two species are slight.

It is estimated that 100,000 new cases of this disease occur annually within the rapidly growing population of people who live in regions of the United States between southwest Texas and southern California, where the disease is endemic (Galgiani, J. N. Coccidioidomycosis: A regional disease of national importance; rethinking our approaches to its control. Annals of Internal Medicine. 1999. 130:293-300). Although the majority of immunocompetent individuals are able to resolve their *Coccidioides* spp. infection spontaneously, the level of morbidity associated even with the primary form of this respiratory mycosis warrants consideration of a vaccine against the disease. Immunocompromised patients, including those infected with human immunodeficiency virus, are at high risk to contract disseminated coccidioidomycosis (Ampel, N. M., C. L. Dols, and J. N. Galgiani. Results of a prospective study in a coccidioidal endemic area. American Journal of Medicine. 1993. 94:235-240). It is also apparent from results of several clinical studies that African-Americans and Asians are genetically predisposed to development of the potentially fatal, disseminated form of the respiratory disease (Galgiani, J. N. 1993. Coccidioidomycosis. Western Journal of Medicine 159:153-171).

The rationale for commitment of research efforts to develop a *Coccidioides* spp. vaccine is based on clinical evidence that individuals who recover from the respiratory coccidioidomycosis disease retain effective long-term cellular immunity against future infections by the pathogen (Smith, C. E. 1940. American Journal of Public Health 30:600-611). In addition, early preclinical studies demonstrated that a formalin-killed whole-cell (spherule) vaccine prevented deaths in mice after infection with even very large numbers of coccidioidal spores (Levine et al. 1961. Journal of Immunology 87:218-227). However, when a similar vaccine preparation was evaluated in a human trial, there was substantial local inflammation, pain, and induration at the injection site, rendering the vaccine unacceptable (Pappagianis et al. Evaluation of the protective efficacy of the killed *Coccidioides immitis* spherule vaccine in humans. American Review of Respiratory Diseases. 1993. 148:656-660). Further, there was no difference in the number of cases of coccidioidomycosis or the severity of the disease in the formalin-killed spherule vaccinated group compared to the placebo group. Therefore, the original human vaccine trial was not successful.

Subsequent attempts to develop a coccidioidal vaccine focused on crude or partially purified subcellular preparations from the fungus, and had limited success in experimental models (Zimmermann, C. R., S. M. Johnson, G. W. Martens, A. G. White, B. L. Zimmer, and D. Pappagianis. Protection against lethal murine coccidioidomycosis by a soluble vaccine from spherules. Infection and Immunity. 1988. 66:2342-2345; Lecara, G., Cox, R. A., and Simpson, R. B. *Coccidioides immitis* vaccine: potential of an alkali-soluble, water-soluble cell wall antigen. Infection and Immunity. 1983. 39: 473-475; Cole, G. T., T. N. Kirkland, and S. H. Sun. An immunoreactive, water-soluble conidial wall fraction of *Coccidioides immitis* 1987. Infection and Immunity 55:657-667; Cole G. T., Kirkland T. N., Franco M., Zhu S., Yuan L., Sun S. H., Hearn V. M. Immunoreactivity of a surface wall fraction produced by spherules of *Coccidioides immitis*. Infection and Immunity 1988 October; 56:2695-701).

There is a long felt need for a more effective and usable treatment or vaccination regimen to prevent, treat, or ameliorate infection of *Coccidioides* spp. and disease states associated with the infection.

SUMMARY OF THE INVENTION

Accordingly, it is an object herein to provide the methods for identifying and isolating nucleic acids encoding polypeptides of *Coccidioides* spp. that have an immunostimulatory activity. Such immunostimulatory nucleotides and polypeptides will be useful in the prevention, treatment, and diagnosis of infections due to *Coccidioides* spp.

In order to meet these needs, the present invention provides compositions and methods for the production of polypeptide antigens of *Coccidioides* spp.

The present invention is directed to polynucleotides encoding the antigens. The antigens may be produced by recombinant technology from the CSA gene. The present invention is also directed to gene fragments derived from the CSA gene *Coccidioides posadasii*, including but not limited to the polynucleotide sequences of SEQ ID NO: 1 and SEQ ID NO:3.

In one embodiment, the polypeptide of the present invention encompasses the full-length 166 amino acid fusion protein sequence depicted in SEQ ID NO:4. In another embodiment, the present invention is directed to polypeptide that lacks the N-terminal amino acids 1-20 of SEQ ID NO:4.

The present invention also provides the use of Csa polypeptides and polynucleotides encoding the polypeptides to elicit an immune response sufficient to provide an effective immunization against *Coccidioides* spp. infection. In one embodiment, the polypeptides provide protection against *Coccidioides posadasii* and/or *Coccidioides immitis* infections in a mammal, such as a human. In another embodiment, the polypeptides provide protection against *Coccidioides* spp. infection in domestic animals, including but not limited to dogs, cats, horses, and cattle. In a further embodiment, the invention provides polynucleotides encoding Csa polypeptides in a vector suitable for transforming human cells as a method for immunizing humans against *Coccidioides* spp. infection.

The present invention further provides the use of Csa polypeptides in combination with one or more other *Coccidioides* spp. polypeptides to elicit an immune response sufficient to provide an effective immunization against *Coccidioides* spp. infection. In one embodiment the polypeptides are provided as a composition containing a mixture of said polypeptides. In another embodiment, the composition is provided as a single fusion polypeptide comprised of the *Coccidioides* spp. polypeptides.

The invention also provides expression vectors that include regulatory sequences such as promoters or other transcriptional regulatory elements operably linked to the nucleotide sequences that control expression of the nucleotide sequences or degenerate variants of the sequences in host cells for the production of the Csa polypeptides of SEQ ID NO:4 and or SEQ ID NO:2.

The invention further provides host cells derived from yeast, bacterial, plant, animal or human sources containing the expression vectors comprising the sequences of SEQ ID NO: 1. Additionally, the invention provides host cells derived from yeast, bacterial, plant, animal or human sources containing the expression vectors comprising the sequences of SEQ ID NO:3.

The present invention also provides shorter polypeptide fragments included within amino acids 1 to 166 and/or amino acids 21-166 of SEQ ID NO:4, and polypeptides within amino acids 1 to 146 of SEQ ID NO: 2. Therefore, these shorter polypeptides may include polypeptides of not less than 25 amino acids in length, inclusive of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78-100 amino acids in length. Such polypeptide fragments, which are substantially the same amino acid length, provide similar ability to elicit an immune response, including such immune responses that provides protection against *Coccidioides* spp. infection.

In another embodiment, the present invention includes polypeptides which are substantially identical to the polypeptides in SEQ ID NO:4 and or SEQ ID NO:2 and or contain at least one conservative substitution. Such polypeptides, which are substantially the same amino acid length, provide similar ability to elicit an immune response, including such immune responses that provides protection against *Coccidioides* spp. infection. Such polypeptides having substantial identity to the polypeptides in SEQ ID NO:4 and or SEQ ID NO:2, include those polypeptides having at least 99%, at least 95%, at least 90%, at least 85%, at least 80%, at least 75%, and at least 70%; and which have the aforementioned activities.

The present invention further provides methods and compositions containing isolated polypeptides identical or substantially identical to the polypeptides in SEQ ID NO:4 or SEQ ID NO: 2, the compositions find use as pharmaceutical compositions.

The present invention also provides vaccine formulations and methods of preparing the formulations containing the Csa polypeptides and or polynucleotides encoding the polypeptides. The present invention further provides vaccine formulations containing adjuvants and pharmaceutical excipients and carriers.

The present invention provides the Csa vaccine formulations and methods for eliciting an effective immune response in a mammal, including humans and domestic animals, for the prevention of *Coccidioides* spp. infections.

The present invention further provides kits containing the Csa polypeptides and or polynucleotides encoding the polypeptides, to facilitate the use of the polypeptides and or polynucleotides.

The present invention also provides a promoter sequence including the promoter of the Csa gene, which can direct gene expression in *Coccidioides* spp. as well as in other microorganisms such as *E. coli* or *Saccharomyces cerevisiae*.

The present invention also provides the use of the Csa polypeptides and or polynucleotides encoding the Csa polypeptides in diagnostic kits for the detection of infections due to *Coccidioides* spp. in mammals, such as humans and domestic animals.

The present invention also provides an antibody specific for an antigen of the Csa polypeptide and methods for the creation of such antibodies. Such antibodies may be used in diagnostic kits for the detection of infections due to *Coccidioides* spp. The present invention provides kits containing antibodies in suitable compositions for the detection of infections due to *Coccidioides* spp. in mammals, such as humans and domestic animals.

The above and other aspects of the invention will become readily apparent to those of skill in the art from the following detailed description and figures, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Nucleotide and derived amino acid sequences of the native *C. posadasii* CSA gene [amino acids are displayed in a single-letter abbreviation after alignment for maximal identity by the program CLUSTAL W (PAM 250 matrix)]. The open reading frame (ORF) of CSA deduced from the genomic sequence is not interrupted by introns. The translated amino acid sequence shows a protein of 146 residues after cleavage of the N putative terminal signal sequence (1-69 bp translated as the first 23 amino acids). The full genomic clone sequence is SEQ ID NO: 8. The nucleotide sequence of the CSA gene is SEQ ID NO: 1. The derived amino acid sequence of the CSA gene is SEQ ID NO: 2.

FIG. 2: The aligned nucleotide (SEQ ID NO:3) and derived amino acid sequences (SEQ ID NO:4) of the rCSA gene construct. The translated amino acid sequence shows a protein of 166 amino acid residues; the 20 aa difference between the native Csa and rCsa is due to the fusion peptide at the N-terminal of the rCsa derived from the pET-28b vector. The rCsa polypeptide does not have a signal peptide.

BRIEF DESCRIPTION OF THE SEQUENCE LISTING

SEQ ID NO:1 depicts the determined nucleotide sequence of CSA open reading frame (ORF) including the terminal signal sequence;

SEQ ID NO:2 depicts the derived amino acid sequence of the native Csa polypeptide encoded by the nucleotide sequence of SEQ ID NO: 1;

SEQ ID NO:3 depicts the determined nucleotide sequence of the recombinant construct containing CSA ORF and vector construct sequences that encode a fusion polypeptide. In the present sequence, nucleotides 1 through 60 are derived from the vector pET28b vector and encode an affinity tag, while nucleotides 61 through 501 are derived from the CSA ORF;

SEQ ID NO:4 depicts the derived amino acid sequence of the recombinant Csa fusion polypeptide encoded by the nucleotide sequence of SEQ ID NO:3, including 20 N-terminal amino acids derived from the pET28b vector;

SEQ ID NO:5 depicts the nucleotide sequence of the upstream primer used for subcloning the CSA sequence into the pET28b vector at the NdeI restriction site; and SEQ ID NO:6 depicts the nucleotide sequence of the downstream primer used for subcloning the CSA sequence into the pET28b vector at the SalI restriction site.

SEQ ID NO:7 depicts the nucleotide sequence of the synthetic CpG adjuvant used in animal experiments.

SEQ ID NO: 8 depicts the sequence of the genomic clone depicted in FIG. 1.

DETAILED DESCRIPTION OF THE INVENTION

Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein.

I. The Polypeptide Sequences of the Invention.

The invention focuses on the use of Csa polypeptides and the nucleotide sequences that encode them as immunogenic antigens for a preventative or therapeutic vaccine for coccidioidomycosis, or for detection of immune responses in individuals infected by *Coccidioides* spp.

Native Csa is a glycosylated protein of 146 amino acids that does not contain a GPI-anchor signal but does have a 23 amino acid (aa) signal peptide and a predicted cleavage site at $L^{23}/A^{24}$. The amino acid sequence of native Csa is shown in SEQ ID NO:2. The principle monosaccharides involved in the glycosylation of the native protein are glucose and mannose. The rCsa is a protein of 166 amino acids; the differences between the native Csa and rCsa include the presence of the fusion peptide at the N-terminal of the rCsa (MGSSHHHHHHSSGLVPRGSH)(amino acids 1 to 20 of SEQ ID NO: 4) derived from the pET-28b vector and the lack of a predicted signal peptide in rCsa. The amino acid sequence of rCsa is shown in SEQ ID NO:4. The rCsa polypeptide is immunologically reactive with antisera raised against native Csa, a known antigen of *Coccidioides* spp., as described by Pan et al. (Pan, S, Cole, G. T. Molecular and biochemical characterization of *Coccidioides immitis*-specific (CS) antigen. 1995. Infection and Immunity 63(10): 3994-4002), Cole et al. (Cole, G. T., Starr, M. E., Sun, S. H., Kirkland, T. N. 1986. Antigen identification in *Coccidioides immitis*. In I. L. Leive, P. F. Bonventre, J. A. Morella S. D. Silver, and H. C. Wu (ed.), Microbiology-1986. American Society for Microbiology, Washington, D.C., p 159-164. ), and Cole et al. (Cole, G. T., Zhu, S. W. et al. Isolation of antigens with proteolytic activity from *Coccidioides immitis*. Infection and Immunity. 1989. 57(5): 1524-1534).

As used herein, the terms "protein" or "polypeptide" are used in the broadest sense to mean a sequence of amino acids that can be encoded by a gene or by a recombinant nucleic acid sequence or can be chemically synthesized. A protein can be a complete, full length gene product, which can be a core protein having no amino acid modifications, or can be a post-translationally modified form of a protein such as a phosphoprotein, glycoprotein, proteoglycan, lipoprotein or nucleoprotein. In some cases, the term "polypeptide" is used in referring to a portion of an amino acid sequence (peptides) of a full length protein. An active fragment of a Csa is an example of such a polypeptide. The polypeptide finds use as an antigen. The antigen can be utilized in fragment form. The reasons for reducing the full-length protein antigen to fragments are multiple; 1) it is well-known in the art that there is a positive correlation between development of DTH (delayed-type hypersensitivity) (a Th1 immune response) to coccidioidal antigens and the ability to resist disseminated coccidioidomycosis. This response is generally regarded as a MHC II type response (Louie et al. 1999. Influence of host genetics on the severity of coccidioidomycosis. Emerging Infectious Diseases 5:672-680) and that peptides that bind to MHC II receptors are generally 13-25 residues in length; 2) determination of epitopes within a larger polypeptide or multiple peptides that enhance or suppress an immune response allow for the creation of fusion proteins containing select epitopes that can be used as vaccines with increased potency (Sette A, et al. 2002. Optimizing vaccine design for cellular processing, MHC binding and TCR recognition. Tissue Antigens 59:443-451); 3) reducing the size of the polypeptide can lead to important advantages in the production, purification and safety of a vaccine.

"Consisting essentially of", in relation to amino acid sequence of a polypeptide, protein or peptide, is a term used hereinafter for the purposes of the specification and claims to refer to a conservative substitution or modification of one or more amino acids in that sequence such that the tertiary configuration of the polypeptide, protein or peptide is substantially unchanged.

"Conservative substitutions" is defined by substitutions of amino acids having substantially the same charge, size, hydrophilicity, and or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine.

"Modification", in relation to amino acid sequence of a polypeptide, protein or peptide, is defined functionally as a deletion of one or more amino acids which does not impart a change in the conformation, and hence the biological activity, of the polypeptide, protein or peptide sequence.

The common amino acids are generally known in the art. Additional amino acids that may be included and or substituted in the peptide of the present invention include: L-norleucine; aminobutyric acid; L-homophenylalanine; L-norvaline; D-alanine; D-cysteine; D-aspartic acid; D-glutamic acid; D-phenylalanine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine; D-ornithine; aminoisobutyric acid; L-ethylglycine; L-t-butylglycine; penicillamine; I-naphthylalanine; cyclohexylalanine; cyclopentylalanine; aminocyclopropane carboxylate; aminonorbornylcarboxylate; L-α-methylalanine; L-α-methylcysteine; L-α-methylaspartic acid; L-α-methylglutamic acid; L-α-methylphenylalanine; L α-methylhistidine; L-α-methylisoleucine; L-α-methyllysine; L-α-methylleucine; L-α-methylmethionine; L-α-methylasparagine; L-α-methylproline; L-α-methylglutamine; L-α-methylarginine; L-α-methylserine; L-α-methylthreonine; L-α-methylvaline; L-α-methyltryptophan; L-α-methyltyrosine; L-α-methylornithine; L-αL-α-methylnorleucine; amino-α-methylbutyric acid;. L-α-methylnorvaiine; L-α-methylhomophenylalanine; L-α-methylethylglycine; methyl-β-aminobutyric acid;. methylaminoisobutyric acid; L-α-methyl-t-butylglycine; methylpenicillamine; methyl-α-naphthylalanine; methylcyclohexylalanine; methylcyclopentylalanine; D-α-methylalanine; D-α-methylornithine; D-α-methylcysteine; D-α-methylaspartic acid; D-α-methylglutamic acid; D-α-methylphenylalanine; D-α-methylhistidine; D-α-methylisoleucine; D-α-methyllysine; D-α-methylleucine; D-α-methylmethionine; D-α-methylasparagine; D-α-methylproline; D-α-methylglutamine; D-α-methylarginine; D-α-methylserine; D-α-methylthreonine; D-α-methylvaline; D-α-methyltryptophan; D-α-methyltyrosine; L-N-methylalanine; L-N-methylcysteine; L-N-methylaspartic acid; L-N-methylglutamic acid; L-N-methylphenylalanine; L-N-methylhistidine; L-N-methylisoleucine; L-N-methyllysine; L-N-methylleucine; L-N-methylmethionine; L-N-methylasparagine; N-methylcyclohexylalanine; L-N-methylglutamine; L-N-methylarginine; L-N-methylserine; L-N-methylthreonine; L-N-methylvaline; L-N-methyltryptophan; L-N-methyltyrosine; L-N-methylornithine; L-N-methylnorleucine; N-amino-α-methylbutyric acid; L-N-methylnorvaline; L-N-methylhomophenylalanine; L-N-methylethylglycine; N-methyl-γaminobutyric acid; N-methylcyclopentylalanine; L-N-methyl-t-butylglycine; N-methylpenicillamine; N-methyl-α-naphthylalanine; N-methylaminoisobutyric acid; N-(2-aminoethyl)glycine; D-N-methylalanine; D-N-methylornithine; D-N-methylcysteine; D-N-methylaspartic acid; D-N-methylglutamic acid; D-N-methylphenylalanine; D-N-methylhistidine; D-N-methylisoleucine; D-N-methyllysine; D-N-methylleucine; D-N-methylmethionine; D-N-methylasparagine; D-N-methylproline; D-N-methylglutamine; D-N-methylarginine; D-N-methylserine; D-N-methylthreonine; D-N-methylvaline; D-N-methyltryptophan; D-N-methyltyrosine; N-methylglycine; N-(carboxymethyl)glycine; N-(2-carboxyethyl) glycine; N-benzylglycine; N-(imidazolylethyl)glycine; N-(1-methylpropyl)glycine; N-(4-aminobutyl)glycine; N-(2-methylpropyl)glycine; N-(2-methylthioethyl)glycine; N-(hydroxyethyl)glycine; N-(carbamylmethyl)glycine; N-(2-carbamylethyl)glycine; N-(1-methylethyl)glycine; N-(3-guanidinopropyl)glycine; N-(3-indolylethyl)glycine; N-(p-hydroxyphenethyl)glycine; N-(1-hydroxyethyl)glycine; N-(thiomethyl)glycine; N-(3-aminopropyl)glycine; N-cyclopropylglycine; N-cyclobutyglycine; N-cyclohexylglycine; N-cycloheptylglycine; N-cyclooctylglycine; N-cyclodecylglycine; N-cycloundecylglycine; N-cyclododecylglycine; N-(2,2-diphenylethyl)glycine; N-(3,3-diphenylpropyl)glycine; N-(N-(2,2-diphenylethyl) carbamylmethyl)glycine; N-(N-(3,3-diphenylpropyl) carbamylmethyl)glycine; and 1-carboxy-1-(2,2-diphenylethylamino)cyclopropane.

Because its amino acid sequence has been disclosed by the present invention, the polypeptides of the present invention can be produced by a known chemical synthesis method (for example, a liquid phase synthesis method, a solid phase synthesis method, and others.; Izumiya, N., Kato, T., Aoyagi, H., Waki, M., "Basis and Experiments of Peptide Synthesis", 1985, Maruzen Co., Ltd.) based on that sequence.

The polypeptides of the present invention may contain one or more protected amino acid residues. The protected amino acid is an amino acid whose functional group or groups is/are protected with a protecting group or groups by a known method or by the use of various protected amino acids that are commercially available.

Because native Csa obtained from *Coccidioides* spp. is glycosylated, the polypeptides of the present invention may be provided in a glycosylated as well as an unglycosylated form. Preparation of glycosylated protein or peptide is known in the art and typically involves expression of the recombinant DNA encoding the protein or peptide in a eukaryotic cell (e.g., yeast or mammalian). Likewise, it is generally known in the art to express the recombinant DNA encoding the protein or peptide in a prokaryotic (e.g., bacterial) cell to obtain a protein or peptide, which is not glycosylated. These and other methods of altering carbohydrate moieties on glycoproteins is found, inter alia, in *Essentials of Glycobiology* (1999), Edited By Ajit Varki, Cold Spring Harbor Laboratory Press, Cold Spring Harbor, N.Y., the contents of which are incorporated herein by reference.

II. The DNA Sequences of the Invention.

The protein or peptide of the present invention can be produced by producing a polynucleotide (DNA or RNA) which encodes the amino acid sequence of the protein or peptide of the present invention and producing a protein or peptide by a genetic engineering technique using the polynucleotide. Polynucleotide coding sequences for amino acid residues are known in the art and are disclosed for example in Molecular Cloning: A Laboratory Manual, Third Edition, Sambrook, Fritsch, and Maniatis, Cold Spring Harbor Laboratory Press, 2001.

The originally published sequence of CSA (Pan, S, Cole, G. T. Molecular and biochemical characterization of *Coccidioides immitis*-specific (CS) antigen. 1995, Infection and Immunity 63(10):3994-4002) contained a frame-shift error that has been identified in this invention. The genomic CSA sequence of the present invention has 441 nucleotide residues that encode a polypeptide with 146 amino acids (aa). The genomic sequence encoding CSA is shown in SEQ ID NO: 1. The nucleotide sequence encoding the rCsa of the present invention has 501 nucleotide residues and results in a recombinant polypeptide with 166 aa. The 501 bp nucleotide sequence is shown in SEQ ID NO:3, which includes sequences derived from the pET28b vector.

Within the context of the present invention "polynucleotide" in general relates to polyribonucleotides and polydeoxyribonucleotides, it being possible for these to be non-modified RNA or DNA or modified RNA or DNA. Polynucleotides which encode the peptides of the present invention mean the sequences exemplified in this application as well as those which have substantial identity to those sequences and which encode the peptides. Preferably, such polynucleotides are those which hybridize under stringent conditions as defined herein and are at least 70%, preferably at least 80% and more preferably at least 90% to 95% identical to those sequences. "Consisting essentially of", in relation to a nucleic acid sequence, is a term used hereinafter for the purposes of the specification and claims to refer to sequences of the present invention and sequences with substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the amino acid sequence encoded, are not expected to substantially alter the biological activity of the gene product. Thus, a nucleic acid sequencing encoding a protein or peptide as disclosed herein, may be modified slightly in sequence (e.g., substitution of a nucleotide in a triplet codon), and yet still encode its respective gene product of the same amino acid sequence.

The terms "stringent conditions" or "stringent hybridization conditions" includes reference to conditions under which a polynucleotide will hybridize to its target sequence, to a detectably greater degree than other sequences (e.g., at least 2-fold over background). In particular, a DNA or polynucleotide molecule which hybridizes under stringent conditions is preferably at least 70%, 75%, 80%, 85%, 90%, 95%, 97%, 98% or 99% homologous to the DNA that encodes the amino acid sequences described herein. In a preferred embodiment these polynucleotides that hybridize under stringent conditions also encode a protein or peptide which upon administration to a subject provides an immunostimulation sufficient to provide some level of immune protection against *Coccidioides* spp. as described herein.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides)—for example, "stringent conditions" can include hybridization in 50% formamide, 1 M NaCl, 1% SDS at 37° C., and three washes for 15 min each in 0.1×SSC/1% SDS at 60 to 65° C.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman (Advances in Applied Mathematics. 1981. 2: 482-489), to find the best segment of identity or similarity between two sequences. Gap performs global alignments: all of one sequence with all of another similar sequence using the method of Needleman and Wunsch, (Journal of Molecular Biology. 1970. 48:443-453). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also encompasses DNA segments that are complementary, or essentially complementary, to the sequence set forth in SEQ ID NO:1 and SEQ ID NO:3. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment SEQ ID NO:1 or SEQ ID NO:3 under stringent conditions such as those described herein.

The nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment or fragment of almost any length may be employed, with the total length preferably being limited by the ease of preparation and use in the intended recombinant protocol.

For example, nucleic acid segments or fragments may be prepared that include a short contiguous stretch identical to or complementary to SEQ ID NO:1 or SEQ ID NO:3, such as about a 15, 18 or 21 nucleotide stretch, up to about 20,000, about 10,000, about 5,000 or about 3,000 base pairs in length. Nucleic acid and DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 21, 22, 23, 24, 25, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,001, 20,001 and the like.

It will also be understood that this invention is not limited to the particular nucleic acid and amino acid sequences of SEQ ID NO:1, SEQ ID NO:2, SEQ ID NO:3 and SEQ ID NO:4, respectively. Recombinant vectors and isolated DNA segments may therefore variously include the coding region from SEQ ID NO:3, coding regions bearing selected alterations or modifications in the basic coding region, or they may encode larger polypeptides that nevertheless include such coding regions or may encode biologically functional equivalent proteins or peptides that have variant amino acids sequences.

The nucleic acid and DNA segments of the present invention encode biologically functional equivalent *Coccidioides* spp. polypeptides that arise as a consequence of codon redundancy and functional equivalency that are known to occur naturally within nucleic acid sequences and the proteins thus encoded. Equally, functionally equivalent proteins or peptides may be created via the application of recombinant DNA technology in which changes in the protein structure may be engineered, based on considerations of the properties of the amino acids being exchanged. Changes may be introduced through the application of site-directed mutagenesis techniques, e.g., to introduce improvements to the antigenicity of the protein.

III. Expression Vectors, Hosts, and Expression of Polypeptides of the Invention in vitro and in vivo.

The term "expression vector" refers to a polynucleotide that includes coding sequences that encode the polypeptide of the invention and provides the sequences necessary for its expression in the selected host cell. Expression vectors will generally include a transcriptional promoter and terminator, or will provide for incorporation adjacent to an endogenous promoter. The recombinant host cells of the present invention may be maintained in vitro, e.g., for recombinant protein, polypeptide or peptide production. Equally, the recombinant host cells could be host cells in vivo, such as results from immunization of an animal or human with a nucleic acid segment of the invention. Accordingly, the recombinant host cells may be prokaryotic or eukaryotic host cells, such as *E. coli, Saccharomyces cerevisiae* or other yeast, mammalian or human or plant host cells, although it will be appreciated by the skilled practitioner that other prokaryotic and eukaryotic cells and cell lines may be appropriate for a variety of purposes; e.g., to provide higher expression, desirable glycosylation patterns, or other features. Expression vectors will usually be plasmids, further including an origin of replication and one or more selectable markers. The pET28b-CSA construct of the present invetion is an example of such expression vectors. A Yep-FLAG-1-CSA construct is another example. However, expression vectors may alternatively be viral recombinants designed to infect the host, or integrating vectors designed to integrate at a preferred site within the host's genome. Examples of other expression vectors are disclosed in Molecular Cloning: A Laboratory Manual, Third Edition, Sambrook, Fritsch, and Maniatis, Cold Spring Harbor Laboratory Press, 2001.

Such polynucleotides encoding the polypeptides of the invention and expression vectors carrying the vectors can be used to produce the polypeptides in vitro or in vivo. The polypeptides so produced can be isolated according to the procedures described herein and commonly known in the art and then used in a therapeutic or immunization protocol.

One may also prepare fusion proteins and peptides, e.g., where the *Coccidioides* spp. peptide coding region is included within the same expression unit with other proteins or peptides having desired functions, such as for purification or immunodetection purposes (e.g., proteins that may be isolated by affinity chromatography and enzyme label coding regions, respectively), or proteins and peptides encoding additional antigens capable of eliciting an immunostimulatory response in a subject (e.g., such as the *Coccidioides* spp. polypeptides Ag2/Pra, Ure, Gel1, or other non-*Coccidioides* protein antigens or toxoids, such as tetanus toxoid, diphtheria toxoid, cholera toxoid, ovalbumin, or keyhole limpet haemocyanin).

In another embodiment, the present invention provides polynucleotide based vaccines or immune-stimulatory formulations, whereby the polynucleotide(s) encoding the polypeptides are administered directly to the subject patient in need thereof, provided the polynucleotide has the appropriate transcriptional control regions to direct the expression of the coding sequence contained in the polynucleotide or expression vector.

Therefore, the present invention also provides DNA based vaccines or immunogenic compositions to provide one or more of the polypeptides described herein. DNA vaccines have been developed for a number of diseases, whereby a DNA vaccine contains a DNA encoding an antigen cloned in a plasmid vector. It will be apparent to one skilled in the art that the immunostimulatory activity of the polypeptides encoded by the DNA sequences disclosed herein lies not in the precise nucleotide sequence of the DNA sequences, but rather in the epitopes inherent in the amino acid sequences encoded by the DNA sequences. It will therefore also be apparent that it is possible to recreate the immunostimulatory activity of one of these polypeptides by recreating the epitope, without necessarily recreating the exact DNA sequence. Such sequences may differ by reason of the redundancy of the genetic code from the sequences disclosed herein. Accordingly, the degeneracy of the genetic code further widens the scope of the present invention as it enables major variations in the nucleotide sequence of a DNA molecule while maintaining the amino acid sequence of the encoded protein or a protein that consists essentially of the same sequence. Such degeneracy is described in U.S. Pat. No. 6,228,371, the contents of which are incorporated herein by reference.

The expression of the antigen or protein is effected by providing a strong promoter such as, for example, Rous Sarcoma Virus LTR, the cytomegalovirus immediate early promoter, and the SV40 T antigen promoter. Success with DNA vaccines has been demonstrated using a variety of antigens for a number of diseases (U.S. Pat. Nos. 6,384,018, 6,284,533, 6,165,993, the contents of which are incorporated herein by reference). The DNA vaccine or immune stimulating composition is provided in an acceptable carrier or liposome as described in U.S. Pat. No. 5,703,055, which is incorporated herein by reference; and can be made in accordance with known methods as described in, for example, U.S. Pat. Nos. 5,589,466; 5,580,859; 5,561,064; and 6,339,068, the contents of which are incorporated herein by reference.

The delivery of the DNA vaccine or immunostimulatory composition can be accomplished using a variety of procedures commonly employed in the art. For non-viral DNA transfer in cultured cells, examples of such methods include calcium phosphate mediated, DEAE-dextran, electroporation, direct microinjection, liposome mediated delivery, cell sonnication, and receptor mediated gene targeting which utilize a cell-receptor-specific ligand and an DNA binding agent, which mediate the uptake of a gene into a specific cell type based on the interaction of the ligand and the receptor. The recombinant DNA encoding the polypeptides of the present invention can also be provided to the cells by direct injection of the naked DNA or plasmid DNA or coupled to particle bombardment with known methods as described in, for example, U.S. Pat. No. 5,865,796, incorporated herein by reference.

In another embodied method of delivering the DNA vaccine or immunostimulatory composition to the cell, viral-vector mediated delivery can be used. Examples of viral vectors for such delivery include adeno-associated virus (AAV) (U.S. Pat. No. 5,843,742 incorporated herein by reference), adenovirus (U.S. Pat. Nos. 6,410,010 and 6,403, 370, incorporated herein by reference), vaccinia virus (U.S. Pat. Nos., 6,287,570, and 6,214,353 incorporated herein by reference), herpesvirus, canarypox virus (U.S. Pat. No. 6,183,750 incorporated herein by reference), other Poxviruses, Retrovirus, and other RNA or DNA viral expression vectors known in the art.

The vectors used to deliver the polypeptides of the present invention may be maintained as an episome or stably integrated into the chromosome of the cell.

IV. How the Polypeptide may be Isolated.

The peptides and polypeptides of the present invention when produced, can be purified by protein isolation and purification methods generally known in the field of protein chemistry. Throughout this specification, proteins, polypeptides and peptides are used in interchangeably. Within the context of the present invention, "isolated" means separated out of its natural environment. An "isolated polypeptide" is, in this context, is a substantially pure polypeptide.

The term "substantially pure polypeptide" means a polypeptide which has been separated from at least some of those components which naturally accompany it, such as other contaminating polypeptides, polynucleotides, and or other biological materials often found in cell extracts. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure Csa polypeptide may be obtained, for example, by extraction from a natural source or by expression of a recombinant nucleic acid encoding an immunoreactive Csa polypeptide, such as the nucleic acid molecule shown as SEQ ID NO: 3. In addition, an amino acid sequence consisting of at least an immunogenic portion of the amino acid sequence of SEQ ID NO: 4 can be chemically synthesized in a substantially pure form.

Methods of purification include, for example, extraction, recrystallization, ammonium sulfate precipitation, sodium sulfate, centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, combinations of these, and other know protein or peptide purification methods are well known to those of skill in the art and can be sued herein.

Purity can be measured by any appropriate method, e.g., HPLC analysis, immunoaffinity chromatography using an antibody specific for the Csa polypeptide, polyacrylamide gel electrophoresis, and the like.

A *Coccidioides* spp. polypeptide that is "isolated to homogeneity," as applied to the present invention, means that the *Coccidioides* spp. polypeptide has a level of purity where the *Coccidioides* spp. polypeptide is substantially free from other proteins, peptides and biological components. For example, an isolated *Coccidioides* spp. peptide will often be sufficiently free of other peptide and protein components so that sequencing may be performed successfully or that pharmaceutically acceptable formulations can be created. However, this does not exclude the re-mixing of the peptides of the invention, once isolated, with other vaccine components.

The polypeptides and formulations employing the polypeptides may also be in the form of a peptide salt thereof. In view of the utility of the polypeptides of the present invention, preferred salts include those salts which are pharmaceutically acceptable for administration into a subject patient.

The polypeptides of the present invention may form a salt by addition of an acid. Examples of the acid include inorganic acids (such as hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), etc.

The polypeptides of the present invention may also form a salt with a basic substance. Examples of these basic salts include, for example, salts with inorganic bases such as alkali metal salts (sodium salt, lithium salt, potassium salt, etc.), alkaline earth metal salts, ammonium salts, and the like or salts with organic bases, such as diethanolamine salts, cyclohexylamine salts, and the like.

V. Preparation and Formulation of Vaccines.

In one embodiment of the present invention, the various polypeptides of the present invention may be admixed in various combinations and or admixed with other known proteins or peptides, which are known or believed to facilitate an immunological response thereby providing protection against *Coccidioides* spp. infection. In an alternative embodiment, the polypeptides of the present invention may be administered separately, i.e., at different time points, from each or from other proteins or peptides, which are known or believed to facilitate an immunological response thereby providing protection against *Coccidioides* spp. infection. For example, the peptide of amino acids 1 to 166 of SEQ ID NO:4 can be combined with one or more additional Coccidioides spp. polypeptides or antigens, such as Ag2/Pra, Ure, Gel1, or other non-*Coccidioides* protein antigens or toxoids, such as tetanus toxoid, diphtheria toxoid, cholera toxoid, ovalbumin (OVA), or keyhole limpet haemocyanin (KLH).

The pharmaceutically acceptable carriers which can be used in the present invention include, but are not limited to, an excipient, a stabilizer, a binder, a lubricant, a colorant, a disintegrant, a buffer, an isotonic agent, a preservative, an anesthetic, and the like which are commonly used in a medical field.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like can be used appropriately depending on the administration method, and the polypeptides of the present invention can be accordingly formulated. Pharmaceutical formulations are generally known in the art, and are described, for example, in Chapter 25.2 of Comprehensive Medicinal Chemistry, Volume 5, Editor Hansch et al, Pergamon Press 1990.

The present invention also provides compositions containing the polypeptides or fragments thereof containing one or more suitable adjuvants commonly used in the field of immunology and medicine to enhance the immune response in a subject. Examples of such adjuvants include monophosphoryl lipid A (MPL), a detoxified derivative of the lipopolysaccharide (LPS) moiety of Salmonella minnesota R595, which has retained immunostimulatory activities and has been shown to promote Th1 responses when co-administered with antigens (see U.S. Pat. No. 4,877,611; Tomai et al., Journal of Biological Response Modifiers. 1987. 6:99-107; Chen et al., Journal of Leukocyte Biology 1991. 49:416-422; Garg & Subbarao. Infection and Immunity. 1992.60(6):2329-2336; Chase et al., Infection and Immunity.1986. 53(3):711-712; Masihi et al, Journal of Biological Response Modifiers. 1988. 7:535-539; Fitzgerald, Vaccine 1991. 9:265-272; Bennett et al, Journal of Biological Response Modifiers 1988. 7:65-76; Kovach et al., Journal of Experimental Medicine, 1990. 172:77-84; Elliott et al., Journal of Immunology. 1991.10:69-74; Wheeler A. W., Marshall J S., Ulrich J. T., International Archives of Allergy and Immunology 2001. October; 126(2):135-9; and Odean et al., Infection and Immunity 1990. 58(2):427-432); MPL derivatives (see U.S. Pat. No. 4,987,237) other general adjuvants (see U.S. Pat. No. 4,877,611); CpG and ISS oligodeoxynucleotides (see U.S. Pat. No. 6,194,388; U.S. Pat. No. 6,207,646; U.S. Pat. No. 6,239,116; U.S. Pat. No. 6,339,068; McCluskie, M. J., and H. L. Davis. Vaccine 2002.19:413-422; Ronaghy A, Prakken B J, Takabayashi K, Firestein G S, Boyle D, Zvailfler N J, Roord S T, Albani S, Carson D A, Raz E. Immunostimulatory DNA sequences influence the course of adjuvant arthritis. J Immunol. 2002. 168(1):51-6.; Miconnet et al (2002) 168(3) Journal of Immunology pp 1212-1218; Li et al (2001) Vaccine 20(1-2):148-157; Davis (2000) Devopmental Biology 104:165-169; Derek T. O'Hagan, Mary Lee MacKichan, Manmohan Singh, Recent developments in adjuvants for vaccines against infectious diseases, Biomolecular Engineering 18 (3)(2001) pp. 69-85; McCluskie et al (2001) Critical Reviews in Immunology 21(1-3):103-120); trehalose dimycolate (see U.S. Pat. No. 4,579,945); amphipathic and surface active agents, e.g., saponin and derivatives such as QS21 (see U.S. Pat. No. 5,583,112); oligonucleotides (Yamamoto et al, Japanese Journal of Cancer Research, 79:866-873, 1988); detoxified endotoxins (see U.S. Pat. No. 4,866,034); detoxified endotoxins combined with other adjuvants (see U.S. Pat. No.4,435,386); combinations with QS-21 (see U.S. Pat. No. 6,146,632); combinations of detoxified endotoxins with trehalose dimycolate and endotoxic glycolipids (see U.S. Pat. No.4,505,899); combinations of detoxified endotoxins with cell wall skeleton (CWS) or CWS and trehalose dimycolate (see U.S. Pat. Nos. 4,436, 727, 4,436,728 and 4,505,900); combinations of just CWS and trehalose dimycolate, without detoxified endotoxins (as described in U.S. Pat. No. 4,520,019); chitosan adjuvants (see U.S. Pat. Nos. 5,912,000; 5,965,144; 5,980,912; Seferian, P. G., and Martinez, M. L. Immune stimulating activity of two new chitosan containing adjuvant formulations (2001) Vaccine. 2000. 19(6):661-8). All of the references cited in this paragraph are incorporated herein by reference.

In another embodiment, the antigenic compositions of the present invention can be provided as an adsorbed vaccine or immunostimulatory composition as described in Matheis et al, (Matheis, M., Zott, A., Schwanig, M. The role of the adsorption process for production and control combined adsorbed vaccines. Vaccine. 2000. 20:67-73), which is incorporated herein by reference.

In another embodiment, various adjuvants, even those that are not commonly used in humans, may be employed in animals where, for example, one desires to subsequently obtain activated T cells or to protect valuable or valued animals from infection due to Coccidioides spp.

VI. Administration of Vaccines

As used herein the subject that would benefit from the administration of the polypeptide and or nucleotide vaccines and formulations described herein include any mammal which can benefit from protection against Coccidioides spp. infection. In a preferred embodiment, the subject is a human. In another embodiment, the subject is a domestic animal, including but not limited to dog, cat, horse, bovine (meaning any sex or variety of cattle) or other such domestic animals.

By polypeptides capable of eliciting an immune response in a subject human, including vaccination, the invention covers any polypeptide, peptide, peptide mimic, or chemical product capable of inducing an immune reaction that results in or augments the subject's ability to mount some level of immune protection inhibiting Coccidioides spp. infection. In one embodiment, the Coccidioides spp. is Coccidioides immitis. In another embodiment, the Coccidioides spp. is Coccidioides posadasii.

As used herein, "inhibit", "inhibiting" or "inhibition" includes any measurable reproducible reduction in the infectivity of Coccidioides spp. in the subject patient. "Reduction in infectivity" means the ability of the subject to prevent or limit the spread of Coccidioides spp. fungus in tissues or organs exposed to or infected by said fungus. Furthermore, "amelioration", "protection", "prevention" and "treatment" mean any measurable reproducible reduction, prevention, or removal of any of the symptoms associated with Coccidioides spp. infectivity, and particularly, the prevention, or amelioration of Coccidioides spp. infection and resultant pathology itself.

Optimum doses of polypeptide that elicit an inhibiting response can be determined through experimentation. Typically, one skilled in the art would design such experiments using animal models to test a range of doses that would result in both inhibitory and non-inhibitory responses, allowing for the selection of appropriate doses.

The dosages used in the present invention to provide immunostimulation include from about 0.1 µg to about 500 µg, which includes, 0.5, 1.0, 1.5, 2.0, 5.0, 10, 15, 20, 25, 30, 35, 40, 45, 50, 55, 60, 65, 70, 75, 80, 85, 90, 95, 100, 150, 200, 250, 300, 350, 400, and 450 µg, inclusive of all ranges and subranges there between. Such amount may be administered as a single dosage or may be administered according to a regimen, including subsequent booster doses, whereby it is effective; e.g., the compositions of the present invention can be administered one time or serially over the course of a period of days, weeks, months and or years.

The polypeptide compositions of the present invention can be administered by any suitable administration method including, but not limited to, injections (subcutaneous, intramuscular, intracutaneous, intravenous, intraperitoneal), eye dropping, instillation, percutaneous administration, transdermal administration, oral administration, intranasal administration, inhalation, etc.

VII. Other Uses.

Also included within the scope of the present invention are kits suitable for providing one or more of the polypeptides of the invention. For example, in such a kit one vial can comprise the polypeptides of the invention admixed with a pharmaceutically acceptable carrier, either in a aqueous, non-aqueous, or dry state; and a second vial which can carry immunostimulatory agents, and or a suitable diluent for the peptide composition, which will provide the user with the appropriate concentration of peptide to be delivered to the subject. In one embodiment, the kit will contain instructions for using the polypeptide composition and other components, as included, such instructions can be in the form of printed, electronic, visual, and or audio instructions. The vaccinations will normally be at from two to twelve week intervals, more usually from three to five week intervals. Periodic boosters at intervals of 1-5 years, usually three years, will be desirable to maintain protective levels. The course of the immunization may be followed by assays for activated T cells produced, skin-test reactivity, or other indicators of an immune response.

The polypeptide of the invention can be used to detect the presence of antibodies. in the sera of patients potentially infected with *Coccidioides* spp. Antibodies which react specifically with the inventive polypeptides can be used to detect the presence of circulating antigens in the sera of patients potentially infected with *Coccidioides* spp. Such detection systems include radioimmunoassays and various modifications thereof which are well-know to those skilled in the art. In addition, the polypeptide of the invention can be used to detect the presence of a cell-mediated immune response in a biological sample. Such assay systems are also well-known to those skilled in the art and generally involve the clonal expansion of a sub-population of T cells or the production of cytokines in response to stimuli from the polypeptide or detection of reactive T cells by flow cytometry or other methods known to those skilled in the art; e.g., methods described by Richards et al. (Richards, J. O., Ampel, N. M., Galgiani, J. N. and Lake, D. F.). When so-used, the humoral and or cell-mediated response of a patient can be determined and monitored over the course of the disease. Methods of generating antibodies directed to a specific peptide fragment are known in the art. Examples of such methods are disclosed in Antibodies, A Laboratory Manual, Harlow and Lane, Cold Spring Harbor Press, 1988, herein incorporated by reference.

Having generally described this invention, a further understanding can be obtained by reference to certain specific examples which are provided herein for purposes of illustration only, and are not intended to be limiting unless otherwise specified.

EXAMPLES

Example 1

Cloning, Expression, and Characterization of rCsa

Materials and Methods

The CSA gene of *C. posadasii* (isolate C735) was first isolated from a genomic library constructed in lambda Fix II (Stratagene, San Diego, Calif.) using methods previously described (Wyckoff, E. E., Pishku, E. J., Kirkland, T. N. and Cole, G. T. 1995. Cloning and expression of a gene encoding a T-cell reactive protein from *Coccidioides immitis*: homology to 4-hydroxyphenylpyruvate dioxygenase and the mammalian F antigen. Gene 161:107-111), and was sequenced using the dideoxy chain termination method (Sanger, F., S. Nicklen, and A. R. Coulson. 1977. DNA sequencing with chain-terminating inhibitors. Proceedings National Academy of Science. USA 74:5463-5467) by denatured polyacrylamide gel separation using methods previously described (Pan, S., and G. T. Cole. 1995. Molecular and biochemical characterization of *Coccidioides immitis*-specific antigen. Infection and Immunity 63:3994-4002). The original genomic clone was resequenced using an ABI Prism 310 genetics analyzer (Perkin Elmer, Foster City, Calif.), and examination of the nucleotide sequence was conducted with MacDNASIS Sequence Analysis software (version 3.5, Hitachi, San Bruno, Calif.). We discovered an error in the original nucleotide sequence (duplication of a cytosine at nucleotide position 367; Pan and Cole, 1995), which resulted in a frame shift in the C-terminal region of the translated CSA gene. The revised nucleotide and translated sequences of the CSA gene have been deposited in the GenBank (AY158466). As previously reported (Pan and Cole, 1995), the genomic sequence of the CSA gene lacks introns. The full-length open reading frame (ORF; 438 bp) plus 5' and 3' fragments of the untranslated regions of the gene were amplified by PCR using sense and antisense primers engineered to include restriction sites for ease of subcloning into an expression vector. The nucleotide sequences of these primers are as follows: CSANde; 5'-GGGA<u>CATATG</u>AAGTTCTCACTCCT-3' (SEQ ID NO:5) and CSASal; 5'-GCAC<u>GTCGAC</u>CAATACGCCTTTA-3' (SEQ ID NO:6)(the underlined sequences indicate the NdeI and SalI restriction sites, respectively). The ORF construct was amplified by PCR using the following conditions: the PCR mixture contained 10 ng of *Coccidioides* genomic DNA plus buffer which consisted of 10 mM Tris-HCl (pH 8.3), 50 mM KCl, 1.5 mM MgCl$_2$, 0.2 mM (each) deoxynucleoside triphosphate, 1 µM (each) primers (described above) and 2.5 units of Taq DNA polymerase (Sigma, St. Louis, Mo.) in a total volume of 100 µl. Thirty-five cycles were conducted for amplification of the CSA gene. Initial denaturation was performed at 94° C. for 3 min. Each subsequent cycle consisted of a melting step (94° C., 1 min), an annealing step (60° C., 1 min), and an extension step (72° C., 45 sec). The final extension step of the cycle was conducted at 72° C. for 10 min.

The PCR-amplified 468-bp product was restricted with NdeI and SalI and ligated into the same enzyme restriction sites of the pET28b vector (Novagen, Madison, Wis.). The orientation, frame, and sequence of the plasmid insert was confirmed by DNA sequencing. The pET28b-CSA construct was used to transform *E. coli* strain BL21 (DE3) as described (Guevara-Olvera, L., Hung, C.-Y., Yu, J.-J., and Cole, G. T. 2000. Sequence expression and functional analysis of the *Coccidioides immitis* ODC (ornithine decarboxylase) gene. Gene 242:437-448). The plasmid construct contained a polyhistidine (6×His) sequence at its N-terminus which was derived from the vector. Growth of the transformed cells and induction of expression of the recombinant protein with 0.5 mM isopropyl β-D-thiogalactopyranoside (IPTG) were conducted as previously described (Hung, C.-Y., Yu, J.-J., Lehmann, P. F., and Cole, G. T. 2001. Cloning and expression of the gene which encodes a tube precipitin antigen and wall-associated β-glucosidase of *Coccidioides immitis*. Infection and Immunity 69:2211-2222). The recombinant protein was isolated using a His-Bind Purification Kit (Novagen, Madison, Wis.), performed as previously described (Hung et al., 2001). The purified recombinant Csa protein (rCsa) was subjected to surface-enhanced laser desorption/ionization time-of flight (SELDI-TOF) mass spectrometry to determine its molecular mass. The purified recombinant rCsa was also subjected to Lys-C endoproteinase digestion as reported (Yu, J. J., Smithson, S. L., Thomas, P. W., Kirkland, T. N., and Cole, G. T. 1997. Isolation and characterization of the urease gene (URE) from the pathogenic fungus *Coccidioides immitis*. Gene 198:387-391), followed by peptide profile analysis using matrix-assisted laser desorption/ionization (MALDI; Nilsson, C. L., Puchades, M., Westman, A., Blennow, K., and Davidsson, P. 1999. Identification of proteins in a human pleural exudate using two-dimensional preparative liquid-phase electrophoresis and matrix-assisted laser desorption/ionization mass spectrometry. Electrophoresis 20:860-865). This procedure was performed to confirm that the isolated recombinant protein was the product of expression of the pET28b-CSA plasmid construct. The endotoxin content of the stock solution containing the rCsa protein solubilized in phosphate-buffered saline (0.1 M PBS, pH 7.4) was assayed using a Limulus amebocyte lysate kit (BioWittaker, Walkersville, Md.) following manufacturer's protocol.

Results

The recombinant Csa fusion protein was induced and expressed in E. coli. SDS-PAGE followed by Coomasie blue staining revealed the expression of C. posadasii rCsa protein in the crude E. coli lysate and a highly isolated protein was obtained as a single band by SDS-PAGE following the nickel-affinity chromatographic purification of rCsa.

Analysis of the native C. posadasii CSA gene (SEQ ID NO: 1) predicts a 146 amino acid polypeptide with a molecular mass of 15.6 kDa (Table 1, SEQ ID NO:2). The 23 amino acid N-terminal signal peptide is cleaved, resulting in a polypeptide of 123 amino acids and a molecular weight of 13.2 kDa. The recombinant CSA gene encodes 166 aa polypeptide with a predicted mass of 17.7 kDa (Table 1). The 20 aa difference between the native Csa and rCsa is due to the fusion peptide at the N-terminal of the rCsa derived from the pET-28b vector that encodes the following sequence: MGSSHHHHHHSSGLVPRGSH (amino acids 1 to 20 of SEQ ID NO:4). The rCsa does not have a predicted signal peptide that is cleaved, although it contains the 23 amino acid sequence corresponding to the signal peptide of the native Csa polypeptide. A single, purified band from the SDS electrophoresis corresponding to rCsa was eletroeluted from the SDS-PAGE gel and subjected to SELDI-TOF mass spectrometry to determine its actual molecular size. The estimated molecular weight of the rCsa by this method is 17.7 kDa, which matches the predicted size of the translated CSA gene. The amino acid sequence of rCsa is shown in SEQ ID NO:4 and the nucleotide sequence encoding CSA-pET28b is shown in SEQ ID NO:3. The recombinant Csa protein has an isoelectric point of 6.53, compared to the more acidic 5.43 value derived for native Csa. The rCsa lacks a predicted GPI anchor site. GPI anchor prediction was conducted using the Big-PI Predictor GPI Modification Prediction site, located at univie.ac.at. MALDI-MS analysis of the Lys-C digests of the rCsa confirmed this protein in encoded by the CSA gene. All preparations of the rCsa protein used for animal experiments contained less than 1 endotoxin unit (5 ng of endotoxin) per μg of protein.

TABLE 1

Comparison of various attributes of the native Csa and rCsa

| Features | Native Csa | RCsa |
| --- | --- | --- |
| Molecular weight | 15.6 kDa (146 aa) 13.2 kDa (123 aa)* | 17.7 kDa (166 aa) |
| pI | 5.43 | 6.53 |
| Predicted signal peptide | present | Absent |
| Signal peptide length/cleavage site | 23/L$^{23}$A$^{24}$ | 0 |
| N-glycosylation sites | 0 | 0 |
| Predicted GPI anchor | absent | Absent |

*after cleavage of signal peptide

Example 2

Fungal Burden Immunoprotection Studies

Materials and Methods

Culture conditions. C. immitis (strain RS) was used for all experimental procedures. Cultures were maintained on glucose-yeast extract agar, with arthroconidia prepared from the stock cultures.

Mice. Female, 6-8 week old C57BL/6 mice were purchased from the Jackson Laboratories (Bar Harbor, Me.) and maintained in conventional housing in isolation units.

Immunization and challenge. Three separate experiments were performed. All experiments compared responses in mice immunized with rCsa to those injected with adjuvant control. In experiments 1 and 3, mice were immunized with 5 μg of rCsa plus 10 μg of ISS adjuvant (Trilink Biotechnologies, San Diego, Calif.) or 10 μg of ISS adjuvant as a negative control. In experiment 2, two groups of mice were immunized with either 1 μg or 5 μg rCsa plus ISS adjuvant and one group received ISS adjuvant control. All injections were administered intradermally at the base of the tail in 100 μl volumes on days 0 and repeated on Day 14. On day 28 mice were challenged intraperitoneally with arthroconidia and were sacrificed on day 42. Mice were necropsied and one lung from each animal was removed, homogenized and plated for the quantitative recovery of C. immitis on GYE agar.

Results

The results of the quantitative fungal cultures for the three experients are presented in Table 2. The data indicate that immunization by rCsa, under the conditions of the experiment, led to significant reductions in the fungal burdens in the lungs of at least three log units in comparison to adjuvant controls during the 14 day infection period. Surprisingly, the reductions in Experiment No. 2 were even greater for the lower, 1 μg dose of rCsa, compared to the higher dose.

TABLE 2

Lung fungal burden data

| | Geometric Mean CFU (log 10) ± s.d. (P value vs. control) | | |
| --- | --- | --- | --- |
| Experiment | ISS Control | rCsa 1 μg | rCsa 5 μg |
| 1 | 6.95 ± 1.87 | N.D. | 3.07 ± 1.30 (0.0002) |
| 2 | 6.04 ± 2.25 | 1.98 ± 1.25 (0.0011) | 2.85 ± 1.38 (0.01) |
| 3 | 7.17 ± 1.18 | N.D. | 3.78 ± 0.99 (0.0003) |

N.D.: not done

Example 3

Survival Immunoprotection Studies

Materials and Methods

Culture conditions. C. posadasii (strain C735) was used for all experimental procedures. Stock cultures of the saprobic (mycelial) phase of the fungus were maintained on glucose-yeast extract plates (GYE, 1% glucose, 0.5% yeast extract, 2% agar) by culturing every 30 days. Arthroconidia (asexual reproductive products of the saprobic phase) were harvested from 4 week-old culture plates by passing a suspesion of the cells in sterile PBS solution through an autoclaved glass wool column to remove hyphal fragments. Concentration of viable arthroconidia was determined by dilution plating on GYE agar media.

Mice. Female, 6-week old C57BL/6 mice were purchased from the National Cancer Instute (Bethesda, Md., USA) and maintained in conventional housing under microisolation lids. Mice were immunized one week after receipt. One week before infection, mice were moved to a Biosafety Level 3 laboratory where they remained for the duration of the experiment.

CpG adjuvant. Unmethylated CpG oligonucleotides (Integrated DNA Technologies, Inc, Coralville, Iowa, USA) were used as an immunoadjuvant, as previously described (Li, K., J. J. Yu, C. Y. Hung, P. F. Lehmann, and G. T. Cole. Recombinant urease and urease DNA of *Coccidioides immitis* elicit an immunoprotective response against coccidioidomycosis in mice. Infection and Immunity. 2001. 69:2878-2887; Oxenius, N., M. M. A. Martinic, H. Hengartner, and P. Klenerman. Journal of Virolology. 1999. 73:4120-4126. ). The CpG oligonucleotide sequence used as the adjuvant admixed with rCsa polypeptides or as a control preparation in mice was the following: TCCAT<u>GACGTT</u>CCT<u>GACGTT</u> (CpG motifs are shown underlined) (SEQ ID NO: 7). These oligonucleotides were dissolved in PBS (1 mg/ml) and used as stock solution for subsequent immunizations.

Immunization and challenge. Four groups of mice (10 per group) were immunized subcutaneously (s.c.) with either the control adjuvant (10 µg of CpG prepared in PBS and 50 µl of Incomplete Freund's Adjuvant (IFA) for a total volume of 100 µl ), or with three different amounts of antigen (0.2, 1 or 5 µg rCsa protein, plus adjuvant), as previously described (Li, K., Yu, J.-J., Hung, C.-Y., Lehmann, P. F. and Cole, G. T. Recombinant urease and urease DNA of *Coccidioides immitis* elicit an immunoprotective response against coccidioidomycosis in mice. Infection and Immunity. 2001, 69:2878-2887). The mice were boosted by s.c. immunization 14 days later with the same amount of immunogen plus adjuvant. Mice were challenged with 100 viable arthroconidia of strain C735 by the i.p. route 4 wks after the last immunization and monitored for 60 days for survival.

Results

The results of the survival experiment are presented in Table 3. Control animals experienced a 90% mortality rate by day 37 post-challenge, with no further deaths over the 60-day observation period. Mice immunized with 1 µg of rCsa+adjuvant maintained a 40% survival rate, a statistically significant difference from the control group, and a corresponding increase in mean time to death. The lack of a dose-response effect, as evidenced by reduced survival in the 5 µg rCsa group compared to the 1 µg group, is a reproducible finding with *Coccidioides*-derived antigens, and is comparable to the effects seen in the fungal burden experiments described in Example 2.

As will be recognized by those skilled in the art, in the models described in Examples 2 and 3 in which negative control animals experience such high levels of fungal burden or mortality, the ability of a vaccine preparation comprising a single polypeptide to reduce the fungal burden or prevent deaths over the experimental periods without the intervention of therapeutic antibiotics is a significant finding. As murine models of coccidioidomycosis have long been used by those skilled in the art to evaluate therapeutic and preventative pharmaceutical preparations, the relevance of these findings in human or veterinary coccidioidomycosis is apparent.

TABLE 3

| Survival of mice challenged with *C. posadasii* | | |
|---|---|---|
| Group | % Survival | Mean Survival (Days) |
| Adjuvant Control | 10 | 23.2 |
| rCsa 0.2 µg | 0 | 21.4 |
| rCsa 1 µg | 40 | 34.0 |
| rCsa 5 µg | 20 | 29.3 |

What is claimed is:

1. An isolated nucleic acid comprising the nucleotide sequence of SEQ ID NO:1.

2. An expression vector comprising the nucleic acid of claim 1.

3. The expression vector of claim 2, further conspiring a recombinant regulatory sequence operably linked to said nucleic acid.

4. The expression vector of claim 3, wherein said regulatory sequence is a promoter.

5. The expression vector of claim 3, wherein said regulatory sequence comprises one or more transcriptional regulatory elements that control expression of the nucleic acid in a host cell.

6. The expression vector of claim 5, wherein said host veil is selected from the group consisting of yeast, plant, animal, human and bacterial cells.

7. A host cell comprising the vector of claim 2, wherein said host cell is selected from the group consisting of yeast, plant, animal, human and bacterial cells.

8. An isolated nucleic acid comprising the nucleotide sequence of SEQ ID NO:3.

9. The nucleic acid of claim 8, further comprising at least a second coding region that encodes a second, distinct *Coccidioides* spp. protein, polypeptide or peptide.

10. An expression vector comprising the nucleic acid of claim 8.

11. The expression vector of claim 10, further comprising a recombinant regulatory sequence operably linked to said nucleic acid.

12. The expression vector of claim 11, wherein said regulatory sequence is a promoter.

13. The expression vector of claim 11, wherein said regulatory sequence comprises one or more transcriptional regulatory elements that control expression of the nucleic acid in a host cell.

14. The expression vector of claim 13, wherein said host cell is selected from the group consisting of yeast, plant, animal, human and bacterial cells.

15. A host cell comprising the vector of claim 10, wherein said host cell is selected from the group consisting of yeast, plant, animal, human and bacterial cells.

16. An isolated nucleic acid comprising a nucleotide sequence that encodes a polypeptide with the amino acid sequence of amino acids 21 to 166 of SEQ ID NO:4.

17. An expression vector comprising the nucleic acid of claim 16.

18. The expression vector of claim 17, further comprising a recombinant regulatory sequence operably linked to said nucleic acid.

19. The expression of vector of claim 18, wherein said regulatory sequence is a promoter.

20. A host cell comprising the expression vector of claim 17.

21. The expression vector of claim 18, wherein the regulatory sequence comprises one or more transcriptional regulatory elements that control expression of the nucleic acid in a host cell.

22. The expression vector of claim 21, wherein said host cell is selected from the group consisting of yeast, plant, animal human and bacterial cells.

23. A host cell comprising the vector of claim 17, wherein said host cell is selected from the group consisting of yeast, plant, animal, human and bacterial cells.

24. A vector that (a) infects a human cell and (b) is stably transformed with and expresses a heterologous DNA comprising the nucleotide sequence of nucleotides 61 to 501 of SEQ ID NO:3.

25. The vector of claim 24, wherein said vector encodes a polypeptide, the amino acid sequence of which consists of amino acids 21 to 166 of SEQ ID NO: 4.

* * * * *

SEQUENCE LISTING

```
<160> NUMBER OF SEQ ID NOS: 8

<210> SEQ ID NO 1
<211> LENGTH: 441
<212> TYPE: DNA
<213> ORGANISM: Coccidioides posadasii

<400> SEQUENCE: 1
atgaagttct cactcctcag cgctatcgca gcggctgtct tcgtcccttt cacatccgcc      60
actccacttg ctagcacggc cgacctcagc tacgacactc actacgatga cccatccctg     120
cccctgagtg gcgtcacctg ttctgacggg gacaatggca tgataacaaa gggctacaac     180
accgccggcg agataccaaa ctaccctcac gtcggaggag cttttacggt cgaaacgtgg     240
aacagcccca actgtggaaa gtgctacaaa gtgacataca atgctaaaac gattttttg      300 actgcgatcg accacagcaa ctccggattt aatatcgcga agaagtcgat ggacgtattg     360
acgaacggac gggcagagga attgggcagg atcaaggtga cctacgaaga ggtcgcctcg     420
```

-continued

```
tcgttgtgcg ggttgaaata a                                              441

<210> SEQ ID NO 2
<211> LENGTH: 146
<212> TYPE: PRT
<213> ORGANISM: Coccidioides posadasii

<400> SEQUENCE: 2

Met Lys Phe Ser Leu Leu Ser Ala Ile Ala Ala Ala Val Phe Val Pro
 1               5                  10                  15

Phe Thr Ser Ala Thr Pro Leu Ala Ser Thr Ala Asp Leu Ser Tyr Asp
            20                  25                  30

Thr His Tyr Asp Asp Pro Ser Leu Pro Leu Ser Gly Val Thr Cys Ser
        35                  40                  45

Asp Gly Asp Asn Gly Met Ile Thr Lys Gly Tyr Asn Thr Ala Gly Glu
    50                  55                  60

Ile Pro Asn Tyr Pro His Val Gly Gly Ala Phe Thr Val Glu Thr Trp
65                  70                  75                  80

Asn Ser Pro Asn Cys Gly Lys Cys Tyr Lys Val Thr Tyr Asn Ala Lys
                85                  90                  95

Thr Ile Phe Leu Thr Ala Ile Asp His Ser Asn Ser Gly Phe Asn Ile
            100                 105                 110

Ala Lys Lys Ser Met Asp Val Leu Thr Asn Gly Arg Ala Glu Glu Leu
        115                 120                 125

Gly Arg Ile Lys Val Thr Tyr Glu Glu Val Ala Ser Ser Leu Cys Gly
    130                 135                 140

Leu Lys
145

<210> SEQ ID NO 3
<211> LENGTH: 501
<212> TYPE: DNA
<213> ORGANISM: Coccidioides posadasii

<400> SEQUENCE: 3
atgggcagca gccatcatca tcatcatcac agcagcggcc tggtgccgcg cggcagccat     60
atgaagttct cactcctcag cgctatcgca gcggctgtct tcgtcccttt cacatccgcc    120
actccacttg ctagcacggc cgacctcagc tacgacactc actacgatga cccatccctg    180
cccctgagtg gcgtcacctg ttctgacggg gacaatggca tgataacaaa gggctacaac    240
accgccggcg agataccaaa ctaccctcac gtcggaggag cttttacggt cgaaacgtgg    300
aacagcccca actgtggaaa gtgctacaaa gtgacataca atgctaaaac gatttttttg    360
actgcgatcg accacagcaa ctccggattt aatatcgcga agaagtcgat ggacgtattg    420
acgaacggac gggcagagga attgggcagg atcaaggtga cctacgaaga ggtcgcctcg    480
tcgttgtgcg ggttgaaata a                                              501

<210> SEQ ID NO 4
<211> LENGTH: 166
<212> TYPE: PRT
<213> ORGANISM: Coccidioides posadasii

<400> SEQUENCE: 4

Met Gly Ser Ser His His His His His His Ser Ser Gly Leu Val Pro
 1               5                  10                  15

Arg Gly Ser His Met Lys Phe Ser Leu Leu Ser Ala Ile Ala Ala Ala
```

-continued

```
            20                  25                  30

Val Phe Val Pro Phe Thr Ser Ala Thr Pro Leu Ala Ser Thr Ala Asp
        35                  40                  45

Leu Ser Tyr Asp Thr His Tyr Asp Asp Pro Ser Leu Pro Leu Ser Gly
    50                  55                  60

Val Thr Cys Ser Asp Gly Asp Asn Gly Met Ile Thr Lys Gly Tyr Asn
65                  70                  75                  80

Thr Ala Gly Glu Ile Pro Asn Tyr Pro His Val Gly Gly Ala Phe Thr
                85                  90                  95

Val Glu Thr Trp Asn Ser Pro Asn Cys Gly Lys Cys Tyr Lys Val Thr
            100                 105                 110

Tyr Asn Ala Lys Thr Ile Phe Leu Thr Ala Ile Asp His Ser Asn Ser
        115                 120                 125

Gly Phe Asn Ile Ala Lys Lys Ser Met Asp Val Leu Thr Asn Gly Arg
    130                 135                 140

Ala Glu Glu Leu Gly Arg Ile Lys Val Thr Tyr Glu Glu Val Ala Ser
145                 150                 155                 160

Ser Leu Cys Gly Leu Lys
                165

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gggacatatg aagttctcac tcct                                            24

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gcacgtcgac caatacgcct tta                                             23

<210> SEQ ID NO 7
<211> LENGTH: 20
<212> TYPE: DNA
<213> ORGANISM: Artificial Sequence
<220> FEATURE:
<223> OTHER INFORMATION: Synthetic adjuvant

<400> SEQUENCE: 7
tccatgacgt tcctgacgtt                                                 20

<210> SEQ ID NO 8
<211> LENGTH: 890
<212> TYPE: DNA
<213> ORGANISM: Coccidioides posadasii

<400> SEQUENCE: 8
gaggttctga agacatttgt gatatttgcg aaggtctatt atcggaattg ctatcacact     60
tacccggttg cagaccggga gagggcctgc gttgaggtat ataaacctcg atcatgtctc    120
gcctggagca catccttctc atcacattcc caacggatat cacgactaag atttaatcag    180
```

-continued

| | |
|---|---|
| aacccttgag aaactttctt ataccttcac ctctccgaca cacttcctcc ataacaaaac | 240 |
| tctaaaatcg ggaaagatga agttctcact cctcagcgct atcgcagcgg ctgtcttcgt | 300 |
| ccctttcaca tccgccactc cacttgctag cacggccgac ctcagctacg acactcacta | 360 |
| cgatgaccca tccctgcccc tgagtggcgt cacctgttct gacggggaca atggcatgat | 420 |
| aacaaagggc tacaacaccg ccggcgagat accaaactac cctcacgtcg gaggagcttt | 480 |
| tacggtcgaa acgtggaaca gccccaactg tggaaagtgc tacaaagtga catacaatgc | 540 |
| taaaacgatt tttttgactg cgatcgacca cagcaactcc ggatttaata tcgcgaagaa | 600 |
| gtcgatggac gtattgacga acggacgggc agaggaattg ggcaggatca aggtgaccta | 660 |
| cgaagaggtc gcctcgtcgt tgtgcgggtt gaaataaagg cgtattggtc gacgtgccgc | 720 |
| aatgctgagt gcgatgattt gatatttgtt tggttgaagg ggaggaacct taatgttaaa | 780 |
| cggttttctt tacatttgta atgcatgtgg cgagggatat atgattactc gactggatta | 840 |
| taatatctaa tgctaaattt cgaggtttat cggggactcc gggtcagcct | 890 |